United States Patent [19]

Pistillo

[11] Patent Number: 4,526,196

[45] Date of Patent: Jul. 2, 1985

[54] GAS PRESSURE MEASURING AND REGULATING DEVICE AND METHOD

[75] Inventor: John Pistillo, Cleveland, Ohio

[73] Assignee: Nayan S. Shah, Mentor, Ohio

[21] Appl. No.: 461,267

[22] Filed: Jan. 26, 1983

[51] Int. Cl.$^3$ .................... F16K 37/00; A61M 15/08
[52] U.S. Cl. .................. 137/557; 137/556.6;
137/559; 251/149.1; 251/268; 128/207.15;
604/100
[58] Field of Search .................. 604/97–100;
137/557, 559, 556.6; 128/207.15; 251/268,
149.1; 73/747

[56]  References Cited

U.S. PATENT DOCUMENTS

| 178,492 | 6/1876 | Walter | 251/268 |
|---|---|---|---|
| 3,122,924 | 3/1964 | Pall | 73/747 |
| 3,712,587 | 1/1973 | Specht | 137/556.6 |
| 3,985,141 | 10/1976 | Stanley et al. | 128/207.15 |
| 4,095,476 | 6/1978 | Banon | 73/747 |
| 4,143,853 | 3/1979 | Abramson | 251/149.1 |
| 4,159,722 | 7/1979 | Walker | 137/557 |
| 4,332,254 | 6/1982 | Lundquist | 604/99 |
| 4,370,982 | 2/1983 | Reilly | 604/100 |
| 4,387,879 | 6/1983 | Tauschinski | 251/149.1 |

Primary Examiner—A. Michael Chambers
Attorney, Agent, or Firm—Hill, Van Santen, Steadman & Simpson

[57]  ABSTRACT

A pressure measuring and regulating device and method for measuring and controlling the pressure within an enclosure such as a pressurized cuff of a medical apparatus, e.g. an endotracheal tube, a tracheostomy tube, or the like, includes effecting communication between a chamber in one end of a hollow barrel. Within the bottom of the chamber is disposed a reservoir containing an indicating fluid, such as mercury. The reservoir communicates with an indicating channel which is visible from the exterior of the barrel. The chamber and the reservoir are exposed to the pressures within the enclosure such that the indicating fluid is displaced into the indicating channel to provide an indication of the pressure within the enclosure. An exteriorly operated regulating member is provided for effecting precise adjustment of the chamber pressure and thus the enclosure pressure and which pressure is simultaneously registered in relation to a monitoring scale associated with the indicating channel.

22 Claims, 10 Drawing Figures

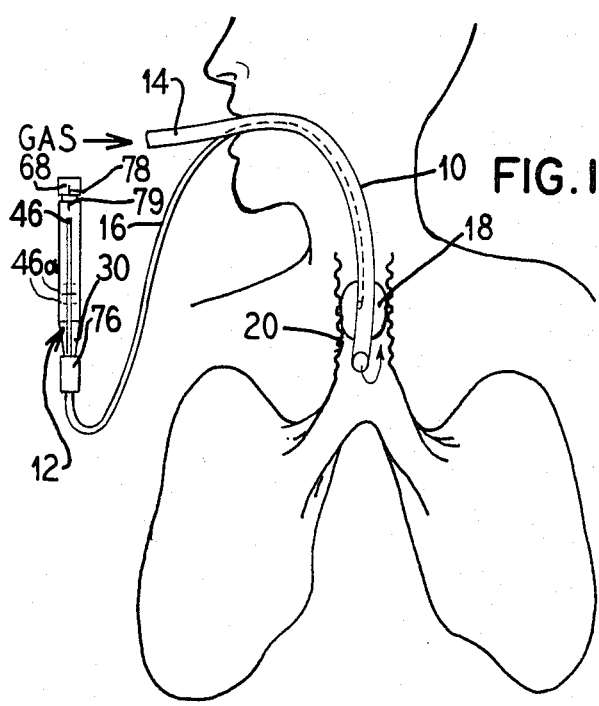
FIG. 1
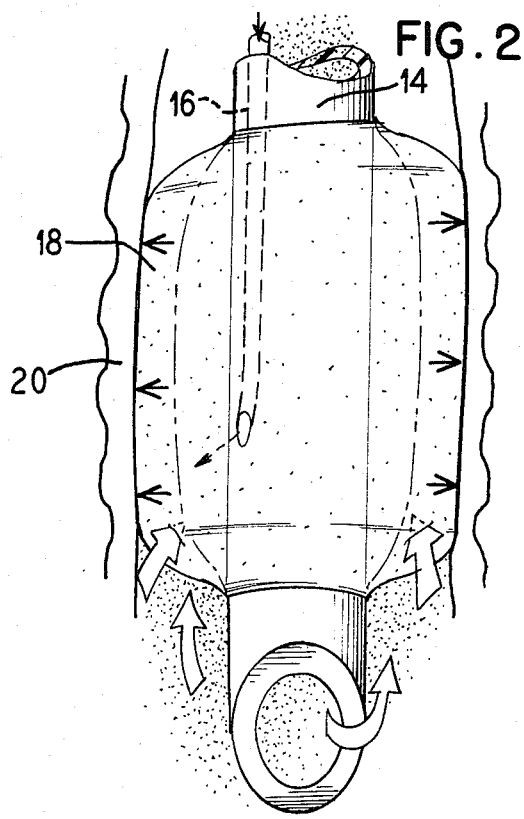
FIG. 2
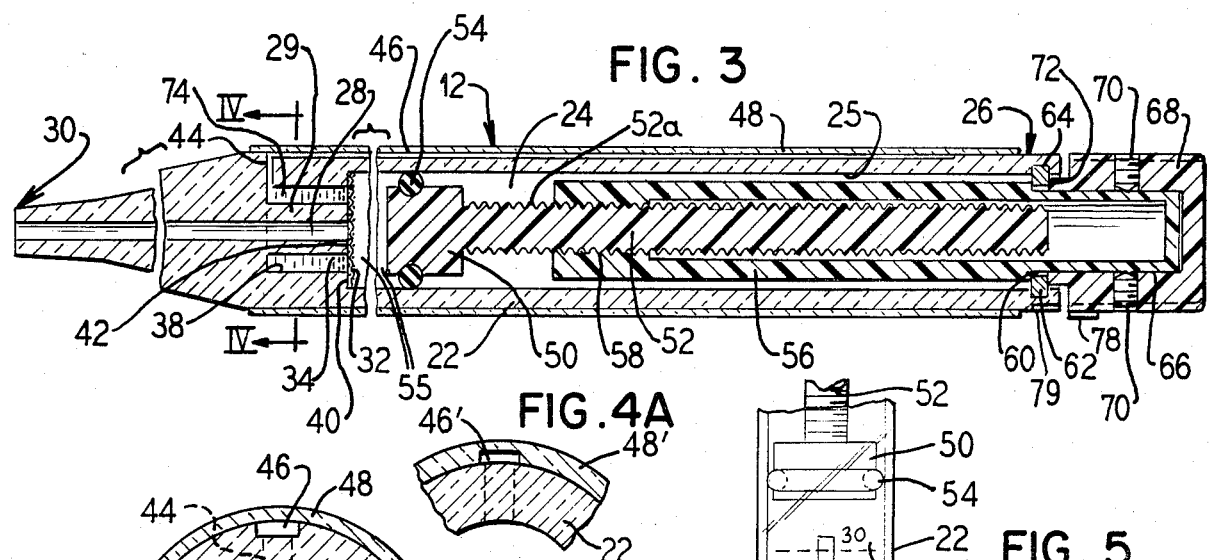
FIG. 3
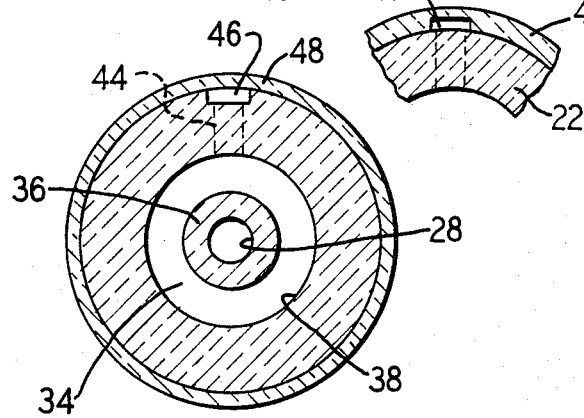
FIG. 4A
FIG. 4
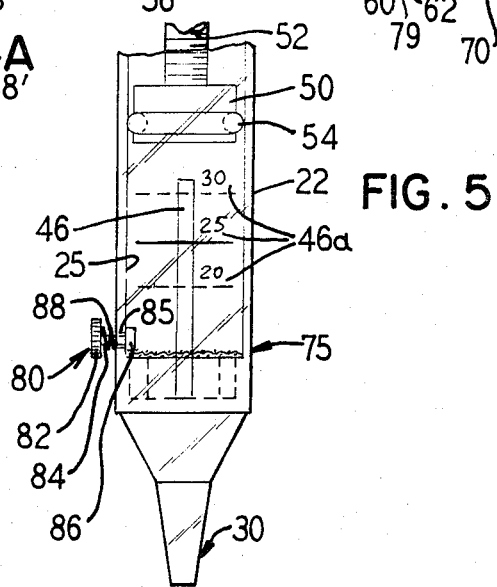
FIG. 5

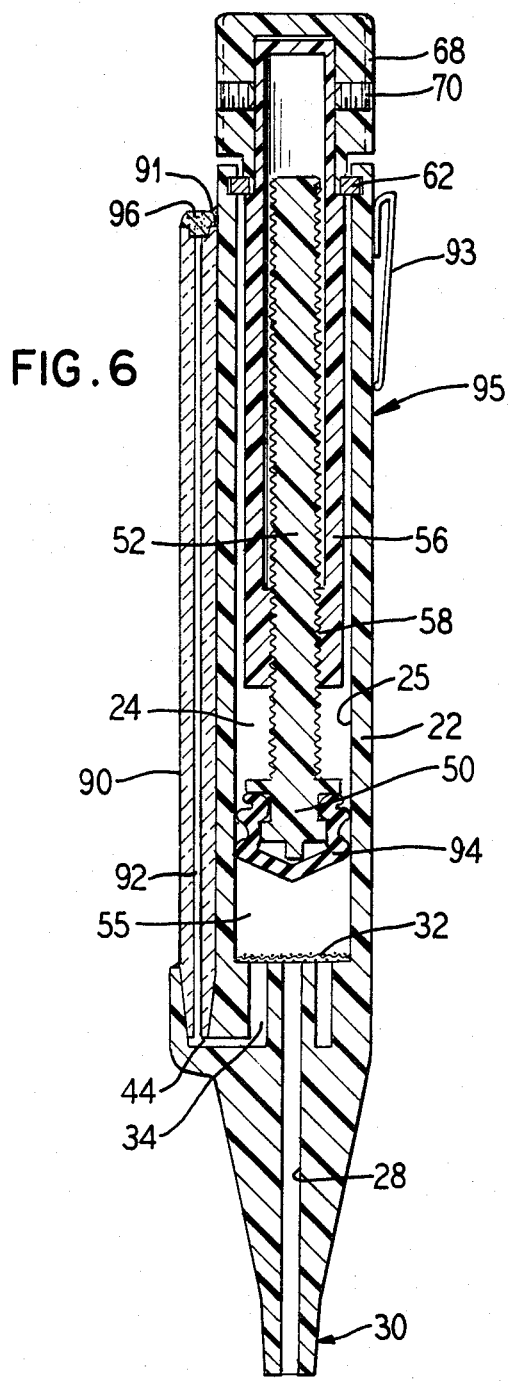
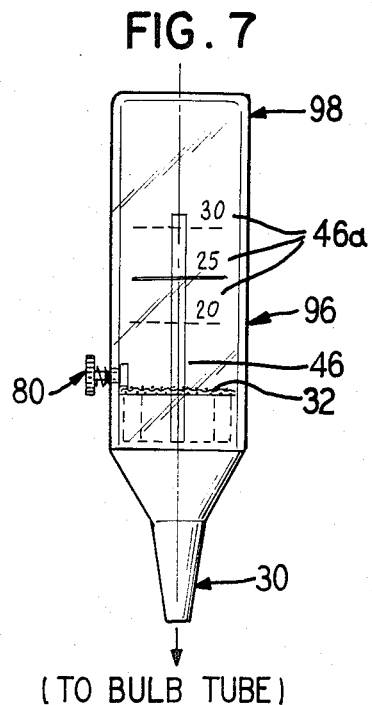
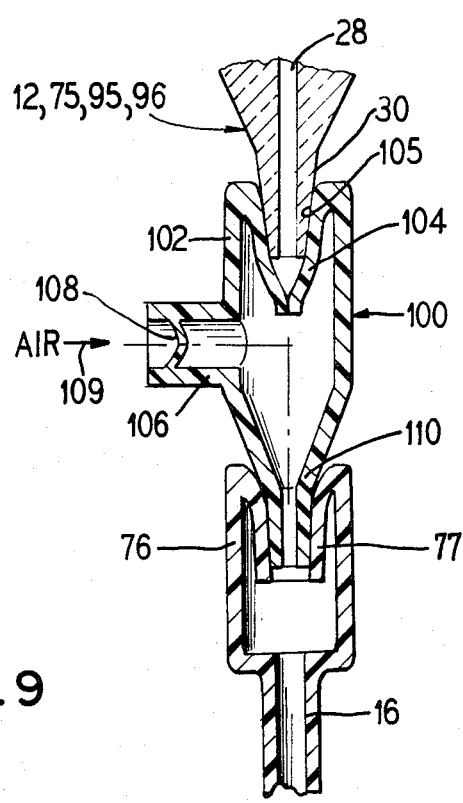
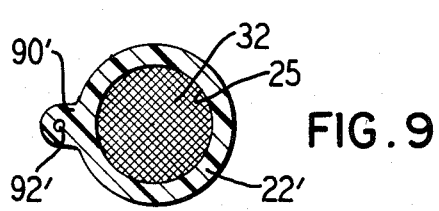

GAS PRESSURE MEASURING AND REGULATING DEVICE AND METHOD

BACKGROUND OF THE INVENTION

The present invention relates generally to pressure measuring and regulating devices and method, and in particular to a device for and a method of measuring and regulating the pressure within an inflatable cuff forming a part of a medical apparatus.

During certain types of surgical procedures, by way of example, anesthetic is administered to a patient by using an endotracheal tube having an inflatable cuff which is inflated by a source of pressurized air. When the cuff is properly inflated, the endotracheal tube is restrained against slippage by the pressure of the cuff against the mucosal wall of the trachea.

However, even though the cuff is made from materials impervious to air, certain types of anesthetics are capable of passing through the walls of the cuff, thereby increasing the gas pressure therein. Often this increase in gas pressure exerted by the over-inflated cuff of the endotracheal tube can result in damage to the mucosal wall of the trachea, which in some instances may be irreversible. Consequently, it is extremely important that the cuff pressure be maintained at a minimum value, e.g. approximately 25 mmHg.

In order to monitor the cuff pressure, mechanical or mercury manometers have heretofore been used. These devices are frequently cumbersome due to their size and occupy valuable space within the operating room, recovery room or even in a patient's room. Moreover, such manometers contain a large amount of dead air space in the connecting tube, and hence the readings are frequently inaccurate.

SUMMARY OF THE INVENTION

According to the present invention, there is provided a new and improved pressure measuring and regulating device and method, the device being small and compact in size and sensitively capable of accurate pressure measurements and pressure regulation.

The pressure measuring and regulating device includes a hollow barrel having a reservoir for an indicating fluid such as mercury, and which is exposed to the pressure of an inflatable cuff. The reservoir is coupled to an indicating channel which is visible from the exterior of the device. The gas pressure acts on the indicating fluid to displace it in the indicating channel by a variable amount dependent upon the magnitude of the pressure. Accordingly, an accurate indication of cuff pressure is developed and is readily observable in the indicating channel.

Pressure regulating means are provided which may be pressure bleed means on the barrel and/or a piston which is sealed against the interior of the hollow barrel and which may be moved within the barrel to control the pressure within the cuff.

The pressure measuring and regulating device may be made of impact resistant materials, such as plastic, and may be made of a size sufficiently small, for instance a pocket pen size, and may have a spring clip to attach the device to the vest or shirt pocket of a user of the device.

Other objects, features and advantages of the present invention will be readily apparent from the following description of certain representative embodiments thereof, taken in conjunction with the accompanying drawings, although variations and modifications may be effected without departing from the spirit and scope of the novel concepts embodied in the disclosure, and in which:

BRIEF DESCRIPTION OF THE DRAWINGS

FIG. 1 is an elevational view partially in phantom of an endotracheal tube in conjunction with the pressure measuring and regulating device of the present invention;

FIG. 2 is an enlarged view of a portion of FIG. 1;

FIG. 3 is a fragmentary longitudinal sectional view of a pressure measuring and regulating device according to the present invention;

FIG. 4 is an enlarged sectional detail view taken substantially along the line IV—IV of FIG. 3;

FIG. 4A is a fragmentary sectional detail view, similar to FIG. 4 but showing an alternative type of indicating channel;

FIG. 5 is a fragmental elevational view of a second embodiment of the invention;

FIG. 6 is a longitudinal sectional view showing a third embodiment of the invention;

FIG. 7 is an elevational view of a fourth embodiment of the invention;

FIG. 8 is a longitudinal sectional view of a connector for use with the present invention; and FIG. 9 is a cross sectional detail view illustrating how the barrel and sight tube of FIG. 6 may be formed in a one piece structure.

DETAILED DESCRIPTION

Referring now to FIGS. 1 and 2, there is illustrated an endotracheal tube 10 in conjunction with a pressure measuring and regulating device 12 constructed according to, and adapted to practice the method of, the present invention.

The endotracheal tube 10 includes a main conduit 14 and an auxiliary tube or duct 16 which is of much smaller diameter than the inside diameter of the main conduit 14 and passes through and along the passage in the main conduit 14 and terminates at one end in communication with an inflatable bulb or cuff 18 which provides a sealed enclosure surrounding the main conduit 14.

In practice, the endotracheal tube 10 is inserted through the mouth of the patient and is advanced into the trachea 20, at which point the inflatable cuff 18 is inflated by coupling the auxiliary duct 16 to a source of pressurized air. The inflatable cuff 18 is inflated to a predetermined pressure to lodge the tube 10 within the trachea 20 and to prevent slippage of the tube 10 therein.

Anesthetic may then be delivered to the lungs of the patient through the main conduit 14. It has been found that for various reasons the pressure in the cuff increases causing possible problems for the patient. For instances, one reason the pressure in the cuff may increase is due to the composition of the cuff 18, wherein anesthesia, over a period of time, may pass through the walls thereof and hence pressures within the cuff 18 could rise, as indicated schematically by the arrows in FIG. 2. If the pressure within the cuff 18 is allowed to rise, damage may be done to the mucosal wall of the trachea. In some cases, the damage may be irreversible. Therefore, it is of utmost importance that cuff pressures be maintained at a minimum, e.g. approximately 25 mmHg.

The present invention allows precise monitoring of pressures within the inflatable cuff 18 and allows precise regulation thereof so as to avoid possible injury resulting from overinflation.

Referring now to FIGS. 3 and 4, in one embodiment the pressure measuring and regulating device 12 comprises housing means including a cylindrical hollow tubular barrel 22 which has an inner chamber bore 24 defined by a cylindrical wall 25, the bore 24 being open at a head end 26 of the barrel 22. The bore 24 communicates at a base end of the barrel 22 with a gas passage conduit 28 defined in part by a tubular generally axially inwardly projecting short stem extension 29. From the extension 29, the conduit 28 extends outwardly through a base end or coupling terminal portion 30 which is part of the housing means of the barrel 22. The base end 30 of the barrel 22 is tapered to form a male luer fitting element for reasons which will become evident in later portions of this specification.

A filter 32, such as a microporous membrane, is interposed between the inner bore 24 and the inner end of the conduit 28. The filter 32 is also disposed between the inner bore 24 and a reservoir 34 which surrounds the inwardly directed conduit extension 29 through which the inner portion of the conduit 28 extends. The reservoir 34 includes an outer cylindrical wall 38 which has a diameter less than the diameter of the wall 25. An axially inwardly facing stepped surface 40 is thereby formed at the juncture of the wall 25 and the outer cylindrical wall 38 of the reservoir 34. The filter 32 is secured to the stepped surface 40 and to inner end 42 of the conduit extension 29. The reservoir 34 is connected through a lateral port 44 to an indicating or sighting channel 46 which may be formed within and extends lengthwise along the outer periphery of the barrel 22.

The barrel 22 is covered by a cylindrical, preferably transparent sheath 48 which may be a length of shrink-fit tubing which is stretched over the barrel 22 and heated so that it contracts and seals against the outer periphery of the barrel 22. The indicating channel 46 is thereby encapsulated by the sheath 48. It is contemplated that the indicating channel 46 may be formed in the wall of the barrel 22 at the time that the barrel is formed. The base end portion of the channel 46 is plugged and sealed up to the point where the passageway or port 44 from the reservoir 34 intersects the channel.

Alternatively, as shown in FIG. 4A, the indicating channel 46' may be formed in a thicker sheath 48' instead of the barrel 22, if desired. For this purpose, the sheath 48 may take the form, of a cylindrical hollow preformed tube having an inner diameter approximately the same size as the outer diameter of the barrel 22 and secured thereto by adhesive or other means.

A piston 50 is slidably disposed within the barrel 22 and has associated therewith means for reciprocatingly actuating the piston, in this instance including an elongate threaded connecting shank portion 52 which extends toward the head end 26 of the barrel 22. Disposed about the periphery of the piston 40 is a sealing means 54 in the form of an O-ring which may be made of rubber or other resilient material. The O-ring 54 should be in compression between the piston 50 and the wall 25 to prevent the passage of gases past the piston 50 to or from a pressure chamber 55 defined between the piston and the screen 32, when the piston is advanced or retracted within the barrel 22.

Threads 52a of the shank 52 are threadably engaged by an elongate hollow piston actuator tube 56 which includes tapped threads 58 within a bore at its inner end through which the shank 52 extends. The actuator tube 56 includes adjacent to its outer end an outer peripheral, axially outwardly facing annular stepped shoulder 60 which bears against a retainer ring 62 engaged within a peripheral radially inwardly facing annular groove 64 in the head end portion of the wall 25 of the barrel 22. The retainer ring 62 is constructed of spring-type material such as a split resililent ring so that it is capable of being compressed in a radial direction to allow insertion thereof into the peripheral channel 64, with the retainer ring expanding to its original diameter, once the compressive force is removed, to secure the ring 62 in place.

The hollow tube 56 also includes a reduced diameter head end portion 66 extending axially outwardly from the stepped shoulder 60 and outwardly beyond the head end of the barrel 22. A preferably cylindrical knurled knob 68 is fixedly secured to the reduced diameter head end portion 66 by means of set screws 70 such that a reduced diameter axially inwardly facing abutment shoulder terminal 72 of the knob 68 slidably contacts the retainer ring 62. The set screws 70 act to connect the knob 68 and the threaded tube 56 corotatably.

Contained within the reservoir 34 is a quantity of indicating fluid, such as mercury 74. The mercury is capable of passing through the port 44 and into the indicating channel 46 in response to gas pressure within the chamber 55 at the axially inner side of the piston 50. It should be noted that the filter 32 provides barrier means which is gas permeable and thus permits gas pressure transmission to the mercury 74 but is impermeable to the mercury and hence the mercury cannot escape into the chamber 55.

In practice, the cuff 18 of the endotracheal tube 10 is inflated by means of a source of pressurized air (not shown) through the auxiliary conduit 16, which has disposed on its outer end a luer adapter 76 which includes a one-way expansible and self-closing resilient valve 77 (FIG. 8), e.g. a duckbill valve.

Once the cuff 18 is properly inflated, the source of pressurized air is removed from the luer adapter 76. To monitor the pressure in the cuff 18, the tapered tip terminal end 30 of the barrel 22 is adapted to be inserted into the adapter 76. The pressure measuring and regulating device 12 should be held substantially vertically for the most accurate pressure readings. The pressurized gases within the cuff 18 are thereby communicated via the conduit 28 and the inner bore chamber 55 to the reservoir 34. The mercury contained within the reservoir 34 is displaced, in response to the cuff pressure transmitted to the chamber 55, outwardly through the port 44 and as a mercury column into the indicating channel 46 which is visible through the sheath 48. An indication of the pressure within the cuff 18 is thereby obtained by visually inspecting the height of the mercury column within the indicating channel 46. Pressure gauge scale indicia markings 46a (FIGS. 1,5 and 7) may be applied to the sheath 48 adjacent to the indicating channel 46 to allow direct readings of pressures within the cuff 18. In this instance, the scale indicia 46a are calibrated for gas pressure mercury displacement in the sighting channel 46, e.g. 20, 25 and 30 mmHg, with the 25 mmHg prominently identified as optimal cuff pressure condition.

The gas pressure within the cuff 18 may be varied by means of the piston 50, actuated by manipulating the knob 68. Since the knob 68 is immovable relative to the hollow threaded tube 56, rotation of the knob 68 causes a corresponding rotation of the tube 56, in turn causing the tube to rotate relative to the threaded connecting stem portion 52 of the piston 50. Since the tube 56 and knob 68 each slidably abut opposite sides of the retainer shoulder ring 62, they cannot move axially within the inner bore 24. Therefore, when the knob 68 is rotated, the hollow tube 56 rotates about the threaded connecting stem portion 52 which with the piston 50 is held adequately against rotation by reason of the frictional engagement of the O-ring 54 with the barrel wall 25, but the piston 50 is movable axially within the bore 24 by virtue of the threaded force transmission coupling provided by the stem threads 52a and the actuator tube threads 58.

Since the O-ring 54 does not permit the passage of gases past the piston 50, axial movement of the piston 50 causes a variation of the pressure of the gas within the chamber 55, the conduit 28 and the inflatable cuff 18. For example, advancement of the piston 50 toward the reservoir 34 will cause an increase in pressure of the gas within the inflatable cuff 18, and, conversely, movement of the piston toward the knob 68 will cause a decrease in the gas pressure within the cuff 18. Hence, if the pressure reading is indicated in the channel 46 as higher than desired, the knob is turned to move the piston toward the knob 68 reducing the pressure in the cuff and reducing the pressure reading in channel 46 until the proper pressure and proper reading are attained. Means for facilitating accurate pressure setting of the piston 50 may be present as calibrated indicia comprising an index element 78 (FIGS. 1 and 3) on the perimeter of the knob 68 registrable with graduated cicumferentially spaced calibrations 79 on the head end of the barrel 22.

Referring now to FIGS. 5-8, further embodiments of the invention are illustrated wherein like numerals refer to like structures throughout.

The embodiment illustrated in FIG. 5 differs from that shown in FIGS. 1-4 in that the device 75 has a manually actuable valve 80. The valve 80 is used to reduce excessively high pressures in the cuff or to more rapidly deflate the cuff 18 without the necessity of rotating the knob 68. The valve 80 includes an external actuating knob 82 which is connected to a valve stem 84, which extends inwardly through a pressure relief port 85 in the wall of the hollow barrel 22. An enlarged valve head 86 is disposed on the inner end of the valve stem 84 within the chamber 55 and is normally biased against the wall 25 in sealing relation about the port 85 by means of a spring 88 located between the actuating knob 82 and the outer wall of the hollow barrel 22. Hence, the chamber 55 is normally sealed off from the exterior of the hollow barrel 22.

When the actuating knob 82 is depressed, overcoming the biasing of the spring 88, the enlarged sealing head 86 moves away from the wall 25, thereby allowing the gases within the chamber 55 to escape through the port 85 to reduce the pressure in the cuff 18 more rapidly than by using the piston 50. In usual practice, if the pressure is too high the valve 80 may be used to initially reduce the pressure somewhat, whereupon the piston 50 may be used to fine adjust the pressure to the precise level.

In the embodiment shown in FIG. 6, the indicating channel 46 and the sheath 48 are omitted from the device 95 and a sight-glass tube 90 is substituted therefor. The tube 90 may be secured by suitable means, such as adhesive 91, to the side of the hollow barrel 22. The glass tube 90 includes an indicating channel 92 which serves the same purpose as the indicating channel 46 in the embodiment shown in FIG. 3. The mercury column channel 92 communicates with the reservoir 34 by means of the port 44, as noted herein before. A spring clip 93 may be secured to the outer wall of the device 95 which can be used to carry the device in a pocket of a user of the device.

Although the upper end of the channel 92 may be sealed so that air trapped above the mercury column is compressed and thus serves to provide a mercury column return biasing means, in a desirable arrangement the top of the channel 92 is open to ambient atmospheric pressure and air pervious but mercury impervious filter means comprising a plug 96 may be secured to the tube 90 across the top of the channel 92.

The device 95 shown in FIG. 6 differs from that shown in FIGS. 1-4 in that the sealing means for the piston 50 is in the form of an elastomer collar 94 which is similar to those ordinarily utilized in syringes. The collar 94 acts to prevent the passage of gases past the piston 50, similar to the function of the O-ring 54 shown in the embodiment of FIG. 3.

If preferred, as shown in FIG. 9, the indicating channel 92' may be formed as a lumen in an integral peripheral enlargement 90' formed in one piece with the barrel 22' having the cylinder 25 therein.

The embodiment shown in FIG. 7 differs from the first embodiment in that the piston 50, the hollow tube 56 and the knob 68 are omitted from the device 96, and the hollow barrel 22 is sealed at one, i.e. head, end 98. As was shown with respect to FIG. 5, a one-way valve 80 is included to allow the pressure in cuff 18 to be lowered or deflated. However, since no piston arrangement is provided, this apparatus can only be used where it is desired to reduce the pressure in the cuff 18, i.e. the cuff can only be reinflated by a source of pressurized air. The device 96 is a stripped down version of the invention and can be used effectively to reduce the pressure in the cuff, and to monitor the pressure in the cuff as by means of the indicating channel 46 and the pressure gauge scale indicia markings 46a.

Referring now to FIG. 8, there is illustrated a connector 100 which facilitates the connection of a source of pressurized air and the pressure measuring and regulating device 12, 75, 95, 96 to the auxiliary conduit 16 which communicates with the inflatable cuff 18. The connector 100 includes a head end, device-coupling, first receptacle 102 having one-way valve means, such as an inwardly projecting duck-bill self-closing valve 104, which is provided with an outwardly opening socket 105 adapted to receive the tapered terminal end 30 of the pressure measuring and regulating device 12, 75, 95, 96.

The connector 100 further includes a pressure air inlet, hollow branch 106 leading therefrom and having therein a one-way valve means 108 similar to the valve 104. This inlet 106 is adapted to receive a connector from a source of pressurized air (not shown) indicated by the arrow 109.

The connector 100 also includes a forward terminal end male coupling tip portion 110 which is adapted to be received within the valve 77 of the luer adapter 76 of the auxiliary conduit 16.

In practice, pressurized air is introduced into the air inlet 106 and through the self-closing valve 108 and passes through the male connecting terminal tip portion 110 and the auxiliary conduit 16 to inflate the cuff 18. In the absence of the terminal end tip 30 therein, the one-way, self-closing valve 104 functions to prevent the escape of pressurized air through the coupling head, first receptacle 102. It is contemplated that the device 12, 75, 95, 96 may or may not be connected with the cuff during the filling of the cuff. In the event the device 12, 75, 95, 96 is moved forward from the position of FIG. 8 to open the valve 104 so that as air is fed through the inlet 106 to the connector 100 and to the cuff, the air pressure will not only fill the cuff 18 but it will also give a pressure reading to the measuring and regulating device 12. When the desired amount of pressure is indicated in device 12, 75, 95, 96 the source of air is shut off and removed from the connector 100.

In the event the tip 30 of the device 12, 75, 95, 96 is in the position of FIG. 8, out of communication with the cuff 18, while the air inlet 106 is connected with the air source, air will flow to the cuff 18 until the cuff has been fully inflated. At this point the source of pressurized air may be removed from the second receptacle inlet 106. Disconnecting of the connector 100 from the source of pressurized air causes the one-way valve 108 to close, thereby preventing the leakage of pressurized air from the cuff 18.

The pressure measuring and regulating device 12, 75, 95, 96 may then be activated by pushing the tapered end 30 thereof inwardly in the socket 105 and causing the one-way valve 104 to open. The barrel conduit 28 and the pressure chamber 55 in the bore 24 are thereby placed in communication with the pressurized air within the cuff 18. Measurement and regulation of the air pressure within the cuff 18 are then effected as was noted with respect to the various embodiments of the invention.

It should be noted that the pressure measuring and regulating device 12, 75, 95, 96 described hereinabove may be used to detect and regulate pressures in other types of devices and is not limited for use with endotracheal tubes utilizing inflatable cuffs. For example, the present invention may be utilized with tracheostomy tubes or catheters utilizing inflatable cuffs. Alternatively, the present invention may be used to measure and regulate pressures within any type of gas-filled envelope or enclosure, if desired.

The pressure measuring and regulating devices disclosed above may be made of any suitable materials, such as impact-resistant plastic or glass, and may be made of a small size and fitted with a clip so as to be carried within the pocket.

It will be understood that variations and modifications may be effected without departing from the spirit and scope of the novel concepts of this invention.

I claim as my Invention:

1. A device for measuring and regulating the gas pressure in an enclosure, comprising:
   pressure responsive means including a visual pressure indicator and having a coupling terminal;
   a duct communicating with said enclosure and having an adaptor provided with a one-way self-closing valve and adapted to receive said coupling terminal for effecting pressure communication between said pressure responsive means and said enclosure through said duct; and
   a hollow elongate connector adapted to be replaceably coupled at one end to said coupling terminal and at its opposite end to said adaptor, and an inlet opening into said connector intermediate said ends and having a one-way self-closing check valve adapted to be opened by a gas pressure source means inserted into said inlet and to close the inlet when the gas pressure source means is removed.

2. A device according to claim 1, wherein said coupling terminal comprises a luer fitting, said connector having a luer adaptor for receiving said luer fitting, said duct adaptor being a luer adaptor, and said connector having a luer fitting to be received by said luer adaptor of the duct.

3. A device for measuring and regulating the gas pressure within an enclosure, comprising:
   an elongate hollow barrel having a head end and a base end;
   a chamber within at least the base end of the barrel;
   a fitting at said base end of the barrel for communication with the pressure in said enclosure;
   a pressure indicator extending lengthwise on and along the outside of the barrel and having means communicating with said chamber;
   pressure sensitive means in said chamber connected to said pressure indicator by means of said communicating means and reacting to pressure communicated to said chamber through said fitting from said enclosure for operating said pressure indicator for indicating the pressure in said enclosure as reflected in said chamber;
   and manually operable means carried by said barrel for controlling the gas pressure within said chamber, and thereby regulating the pressure in said enclosure in accordance with the controlled pressure in said chamber.

4. A device according to claim 3, wherein said pressure controlling means comprises a piston reciprocative in said barrel, and means manipulative exteriorly of said barrel for operating said piston.

5. A device according to claim 4, wherein said manipulative means comprises a digitally engageable knob, and pressure calibrated indexing means on said knob and said head end of the barrel.

6. A device according to claim 3, wherein said pressure indicator comprises a channel extending between said head end and said base end in a portion of a wall of said barrel.

7. A device according to claim 3, wherein said pressure indicator comprises a transparent tube extending substantially from said base and to said head end.

8. A device according to claim 3, wherein said pressure indicator comprises a channel extending substantially between said base end and said head end, said pressure sensitive means comprising a liquid material, and a pressure relief device on the head end portion of said channel permitting free air passage therethrough but being impervious to said liquid material so that air may freely enter and leave said channel but said liquid material cannot escape through the head end portion of the channel.

9. A device according to claim 3, wherein said pressure indicator comprises a channel extending substantially between said base end and said head end of the barrel, said pressure sensitive means comprising a liquid material in a reservoir in said base end of the barrel, and a port connecting the bottom of said reservoir to the lower end of said channel and providing for communication between the reservoir and the pressure indicator channel.

10. A device according to claim 3, wherein said pressure sensitive means comprises a fluid, said pressure indicator includes a sighting channel extending longitudinally along the barrel for external observation, calibrated pressure gauging means on the barrel associated with said sighting channel, said fluid pressure sensitive means being adapted to provide an indicating column in said channel, and said chamber pressure on said fluid material driving the material into said column.

11. A device according to claim 10, wherein said channel has an upper end open to ambient atmosphere, and air pervious plug means in the top of said channel impervious to said fluid material.

12. A device according to claim 3, said manually operable means comprising a pressure control valve operable externally of said barrel for controlling the pressure in said chamber.

13. A device according to claim 3, wherein said pressure controlling means comprises a piston reciprocative in said barrel, a threaded stem on said piston extending away from said head end of the chamber, an actuator for effecting reciprocating movement of said piston in said barrel and comprising a rotatable hollow tube having a tapped coupling with said stem, and means externally of the barrel manipulatable for rotatably operating said actuator.

14. A device according to claim 3, wherein said pressure sensitive means comprises mercury, a reservoir in the bottom of said chamber for said mercury, and a mercury impervious but gas pervious filter separating said reservoir from said chamber.

15. A device according to claim 3, including a duct leading from said enclosure, an adaptor on said duct and provided with a self-closing valve, and said fitting adapted to be received in said adaptor and when thus received opening said valve, and a passageway through said fitting adapted for effecting communication between said adaptor and said chamber.

16. A device according to claim 3, including a hollow connector having an adaptor for receiving said fitting and providing a pressure communication passage leading from said chamber through said fitting, a fitting on the connector adapted to be received in an adaptor on a duct leading to said enclosure, and an inlet into said connector for removeably receiving air source means and provided with a one-way self-closing valve which remains closed in the absence of the air source means.

17. A device according to claim 3, wherein said fitting comprises a conduit having a stem projecting into said chamber, a reservoir defined about said stem and opening into said chamber and having said pressure sensitive means in the form of mercury in the reservoir, said reservoir being in communication with said pressure indicator, and a filter secured across said reservoir and said stem and permitting gas pressure to pass therethrough between said chamber and said reservoir, but being impervious to the mercury so as to provide a mercury barrier between said reservoir on the one hand and said chamber and said conduit at the inner end of said stem on the other hand.

18. A device for measuring and regulating the gas pressure within an enclosure, comprising:

housing means providing an elongate hollow barrel;

means for connecting a chamber at one end of the barrel in communication with pressure in said enclosure;

a pressure indicator observable from the outside of the housing and having pressure sensitive means at said chamber adjacent to said connecting means for reacting to pressure communicated to said chamber from said enclosure;

means carried by said housing means in association with said barrel for controlling the gas pressure within said chamber, and thereby through said connected means regulating the pressure in said enclosure in accordance with the controlled pressure in said chamber;

said connecting means comprising a conduit having a stem projecting into said chamber;

a reservoir defined alongside said stem and opening into said chamber and having said pressure sensitive means in the form of mercury in the reservoir, said reservoir being in communication with said pressure indicator;

and a filter secured across said reservoir and permitting gas pressure to pass therethrough between said chamber and said reservoir, but being impervious to the mercury so as to provide a mercury barrier between said reservoir on the one hand and said chamber and said conduit at the inner end of said stem on the other hand.

19. A device according to claim 18, wherein said pressure indicator comprises a channel extending between said head end and said base end in a portion of a wall of said barrel.

20. A device according to claim 18, wherein said pressure indicator comprises a transparent tube extending substantially from said base end to said head end.

21. A device according to claim 18, wherein said pressure indicator comprises a channel extending substantially between said base end and said head end, said pressure sensitive means comprising a liquid material, and a pressure relief device on the head end portion of said channel permitting free air passage therethrough but being impervious to said liquid material so that air may freely enter and leave said channel but said liquid material cannot escape through the head end portion of the channel.

22. A device according to claim 18, wherein said pressure indicator comprises a channel extending substantially between said base end and said head end of the barrel, said pressure sensitive means comprising a liquid material in a reservoir in said base end of the barrel, and a port connecting the bottom of said reservoir to the lower end of said channel and providing for communication between the reservoir and the pressure indicator channel.

* * * * *